(12) United States Patent
Butte et al.

(10) Patent No.: US 11,839,619 B2
(45) Date of Patent: Dec. 12, 2023

(54) METHODS FOR TREATMENT OF PEDIATRIC SYSTEMIC MASTOCYTOSIS

(71) Applicant: The Regents of the University of California, Oakland, CA (US)

(72) Inventors: Manish J. Butte, Los Angeles, CA (US); Maria I. Garcia-Lloret, Los Angeles, CA (US); Lisa A. Kohn, Los Angeles, CA (US); Mona M. Liu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 425 days.

(21) Appl. No.: 17/021,032

(22) Filed: Sep. 15, 2020

(65) Prior Publication Data
US 2021/0077503 A1 Mar. 18, 2021

Related U.S. Application Data

(60) Provisional application No. 62/901,061, filed on Sep. 16, 2019.

(51) Int. Cl.
*A61K 31/553* (2006.01)
*A61P 37/02* (2006.01)
*A61K 9/00* (2006.01)

(52) U.S. Cl.
CPC .......... *A61K 31/553* (2013.01); *A61K 9/0053* (2013.01); *A61P 37/02* (2018.01)

(58) Field of Classification Search
CPC .................................................... A61K 31/553
See application file for complete search history.

(56) References Cited

U.S. PATENT DOCUMENTS

| 7,973,031 | B2 | 7/2011 | Griffin et al. |
| 8,222,244 | B2 | 7/2012 | Griffin et al. |
| 8,575,146 | B2 * | 11/2013 | Coutre ............... A61P 27/16 540/545 |
| 10,973,822 | B2 * | 4/2021 | Gandhi ............ A61K 39/39558 |

OTHER PUBLICATIONS

Liu et al., J'nal of Allergy and Clinical Immunology, 7(8) pp. 2929-2931 (2019).*
Bibi et al., Immunology and Allergy Clinics of North America, (May 2014) vol. 34, No. 2, pp. 239-262.*
Gotlib et al., "Efficacy and Safety of Midostaurin in Advanced Systemic Mastocytosis", The New England Journal of Medicine, Jun. 30, 2016, 374:2530-2541.
Liu et al., "Treatment of systemic mastocytosis in an infant with midostaurin", Journal of Allergy and Clinical Immunology: in Practice, Clinical Communications, 7(8):2929-2931, May 2019, DOI:https://doi.org/10.1016/j.jaip.2019.05.032.

* cited by examiner

*Primary Examiner* — Paul V Ward
(74) *Attorney, Agent, or Firm* — Mark S. Cohen; PEARL COHEN ZEDEK LATZER BARATZ LLP

(57) ABSTRACT

Methods for treating pediatric patients with systemic mastocytosis are described by administering midostaurin.

20 Claims, 4 Drawing Sheets

METHODS FOR TREATMENT OF PEDIATRIC SYSTEMIC MASTOCYTOSIS

CROSS REFERENCE TO RELATED APPLICATION

This application claims benefit of U.S. Provisional Patent Application No. 62/901,061, filed Sep. 16, 2019, which is incorporated by reference herein in its entirety.

BACKGROUND

Systemic mastocytosis (SM) is a rare disorder entailing multiorgan accumulation of clonal mast cells that proliferate in a ligand-independent fashion due to somatic mutation of the growth factor receptor Kit. These activated mast cells cause symptoms including pruritus, flushing, and diarrhea depending on which organs are involved.

Mastocytosis in children takes on many forms but is mostly restricted to the skin. Localized collections of mast cells such as urticaria pigmentosa rarely require treatment. More extensive spread of mast cells such as diffuse cutaneous mastocytosis is confined to the skin, and given the generally good prognosis and response to standard therapy, evaluation of bone marrow or extracutaneous biopsies has not been suggested and is often not pursued. There are only exceedingly rare reports of SM in newborns. A recent case series noted the presence of organomegaly in all cases of pediatric SM. There is no approved treatment for SM in children.

It is towards an effective treatment for systemic mastocytosis in the pediatric population that the present invention is directed.

SUMMARY OF THE INVENTION

In one aspect, the invention is directed to a method for treating systemic mastocytosis in a pediatric subject in need thereof, comprising administering to the subject an effective dosing regimen comprising midostaurin.

In some embodiments, the pediatric subject is an infant. In some embodiments, the subject is neonatal.

In some embodiments, the systemic mastocytosis is congenital or prenatal. In some embodiments, the systemic mastocytosis comprises the Kit D816V mutation. In some embodiments, the systemic mastocytosis is indolent.

In some embodiments, the systemic mastocytosis is cutaneous mastocytosis.

In some embodiments, the systemic mastocytosis is indolent systemic mastocytosis, smoldering systemic mastocytosis, systemic mastocytosis with associated hematological neoplasm, aggressive systemic mastocytosis or mast cell leukemia.

In some embodiments, the systemic mastocytosis is not responsive to standard of care therapy. In some embodiments, standard of care comprises antihistamines, cromolyn, montelukast, antibiotics, and corticosteroids.

In some embodiments, the midostaurin is administered twice daily at a dose of 30 mg/m$^2$, 45 mg/m$^2$ or 60 mg/m$^2$, or any combination or regimen thereof. In some embodiments, the midostaurin is administered orally. In some embodiments, the midostaurin is administered as a liquid formulation.

In some embodiments, midostaurin administration reduces or eliminates bullae, skin blistering, flushing, or serum tryptase levels.

In some embodiments, administration of midostaurin is discontinued when clinical improvement occurs. In some embodiments, administration of midostaurin is discontinued when clinical improvement of systemic mastocytosis occurs. In some embodiments, clinical improvement is reduction or elimination of bullae, reduction or elimination of skin blistering, reduction or elimination of skin flushing, or the combination thereof. In some embodiments, administration of midostaurin is discontinued when serum tryptase levels return to near or at baseline values. In some embodiments, administration of midostaurin is discontinued when reduction of elimination of bullae is observed, reduction or elimination of skin flushing is observed, return to near normal or normal levels of serum tryptase occurs, or any combination of any of the foregoing.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A and FIG. 1B show skin findings at 7 months, showing hemorrhagic bullae before starting midostaurin. FIG. 1C and FIG. 1D show skin findings at 10 months, 12 weeks after starting midostaurin. FIG. 1E and FIG. 1F show bone marrow histology showing CD25 staining (FIG. 1E, brown) and tryptase stain (FIG. 1F, brown).

DETAILED DESCRIPTION OF THE INVENTION

Figure 1:
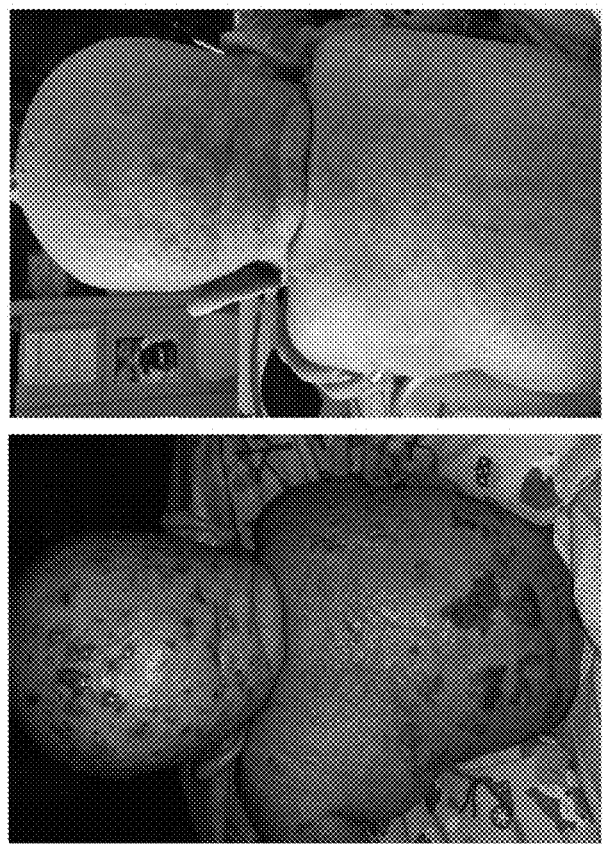
FIG. 1A, FIG. 1B, FIG. 1C, FIG. 1D, FIG. 1E and FIG. 1F show gross and microscopic findings in the patient.

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure, the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value.

Similarly, when values are expressed as approximations, by use of the antecedent "about," it is understood that the particular value forms another embodiment. All ranges are inclusive and combinable. In the context of the present disclosure, by "about" a certain amount it is meant that the amount is within ±20% of the stated amount, or preferably within ±10% of the stated amount, or more preferably within ±5% of the stated amount.

As used herein, the terms "treat", "treatment", or "therapy" (as well as different forms thereof) refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

As used herein, the terms "component," "composition," "formulation", "composition of compounds," "compound," "drug," "pharmacologically active agent," "active agent," "therapeutic," "therapy," "treatment," or "medicament," are used interchangeably herein, as context dictates, to refer to a compound or compounds or composition of matter which, when administered to a subject (human or animal) induces a desired pharmacological and/or physiologic effect by local and/or systemic action. A personalized composition or method refers to a product or use of the product in a regimen tailored or individualized to meet specific needs identified or contemplated in the subject.

The terms "subject," "individual," and "patient" are used interchangeably herein, and refer to an animal, for example a human, to whom treatment with a composition or formulation in accordance with the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys. The compositions described herein can be used to treat any suitable mammal, including primates, such as monkeys and humans, horses, cows, cats, dogs, rabbits, and rodents such as rats and mice. In one embodiment, the mammal to be treated is human. The human can be any human of any age. In an embodiment, the human is an adult. In another embodiment the human is of a pediatric age. In another embodiment the human is 0-18 years of age. In another embodiment, the human is a newborn. In one embodiment, the human is between 0 and 2 months of age. In another embodiment, the human is a newborn. In one embodiment, the human is between 0 and about 2 months of age. In one embodiment, the human is between 0 and 1 year of age. In one embodiment, the human is between 0 and about 1 year of age. In one embodiment, the human is between 0 and 4 years of age. In one embodiment, the human is between 0 and about 4 years of age. In another embodiment, the human is a baby. In one embodiment the human is a child. In one embodiment the human is a toddler. In another embodiment the human is an infant. The human can be male, female, pregnant, middle-aged, adolescent, or elderly. According to any of the methods of the present invention and in one embodiment, the subject is human. In another embodiment, the subject is a non-human primate. In another embodiment, the subject is murine, which in one embodiment is a mouse, and, in another embodiment is a rat. In another embodiment, the subject is canine, feline, bovine, equine, laprine or porcine. In another embodiment, the subject is mammalian.

Conditions and disorders in a subject for which a particular drug, compound, composition, formulation (or combination thereof) is said herein to be "indicated" are not restricted to conditions and disorders for which that drug or compound or composition or formulation has been expressly approved by a regulatory authority, but also include other conditions and disorders known or reasonably believed by a physician or other health or nutritional practitioner to be amenable to treatment with that drug or compound or composition or formulation or combination thereof.

The inventors herein have discovered that pediatric systemic mastocytosis is treatable with midostaurin. There is no approved treatment for systemic mastocytosis in the pediatric population, and only palliative care is available.

Mastocytosis, a type of mast cell disease, is a rare disorder affecting both children and adults caused by the accumulation of functionally defective mast cells (also called mastocytes) and CD34+ mast cell precursors. People affected by mastocytosis are susceptible to a variety of symptoms, including itching, hives, and anaphylactic shock, caused by the release of histamine and other pro-inflammatory substances from mast cells.

Systemic mastocytosis involves the bone marrow in the majority of cases and in some cases other internal organs, usually in addition to involving the skin. Mast cells collect in various tissues and can affect organs where mast cells do not normally inhabit such as the liver, spleen and lymph nodes, and organs which have normal populations but where numbers are increased. In the bowel, it may manifest as mastocytic enterocolitis.

There are five types of systemic mastocytosis: indolent systemic mastocytosis (ISM; the most common SM [>90%]); smoldering systemic mastocytosis (SSM); systemic mastocytosis with associated hematological neoplasm (SM-AHN); aggressive systemic mastocytosis (ASM); and mast cell leukemia (MCL).

Midostaurin (RYDAPT) is a is a multi-targeted protein kinase inhibitor that has been investigated for the treatment of acute myeloid leukemia (AML), myelodysplastic syndrome (MDS) and advanced systemic mastocytosis. It is a semi-synthetic derivative of staurosporine, an alkaloid from the bacterium *Streptomyces staurosporeus*. It is approved in 2017 for treatment of adult patients with newly diagnosed acute myeloid leukemia (AML) that is FLT3 mutationpositive as detected by an FDA-approved test, in combination with standard cytarabine and daunorubicin induction and cytarabine consolidation (1.1); but is not indicated as a single-agent induction therapy for the treatment of patients with AML. It is also indicated for the treatment of adult patients with aggressive systemic mastocytosis (ASM), systemic mastocytosis with associated hematological neoplasm (SM-AHN), or mast cell leukemia (MCL). The indicated dosage for ASM (in adults) is 100 mg orally twice daily with food. In a study on the use of midostaurin in children with relapsed acute leukemia (Zwaan C M, Söderhäll S, Brethon B, Luciani M, Rizzari C, Stam R W, et al. A phase ½, open-label, dose-escalation study of midostaurin in children with relapsed or refractory acute leukaemia. Br J Haematol 2019; 185:623-7) a liquid formulation was used.

Analogues and metabolites of midostaurin may also be used for any of the methods described herein. Analogues and metabolites comprise compounds with the biological activities of midostaurin, such as but not limited to FLT3 tyrosine kinase inhibitory activity and KIT proto-oncogene receptor tyrosine kinase inhibitory activity.

In some embodiments, the midostaurin is administered twice daily at a dose of 30 mg/m$^2$, 45 mg/m$^2$ or 60 mg/m$^2$, or any combination or regimen thereof. In one embodiment, the midostaurin is administered orally. In one embodiment the midostaurin is administered as a liquid formulation. In one embodiment, ondansetron is administered prophylactically before each dose of midostaurin. In one embodiment, standard of care is continued during the administration of midostaurin. In one embodiment, standard of care comprises antihistamines, cromolyn, montelukast, antibiotics, corticosteroids or any combination thereof.

In one embodiment, the dose of midostaurin is given at a dose of 30 mg/m2 twice daily. In some embodiments the dose is increased to 45 mg/m2 twice daily. In some embodiment the dose is increased to 60 mg/m2 twice daily. In some embodiments, the dosing regimen escalates from 30 to 45 to 60 mg/m2 after one week, one month or two months. In some embodiments the midostaurin dosing is continued until clinical improvement is observed. In one embodiment, clinical improvement is resolution of bullae. In one embodiment clinical improvement is a decrease of serum tryptase to normal or near normal levels. In one embodiment, after midostaurin administration is discontinued, the patient is maintained on standard of care therapy. In one embodiment the standard of care therapy is H1 and H2 blockers, cromolyn, montelukast, corticosteroids, or any combination thereof. In one embodiment corticosteroids are weaned after midostaurin administration is discontinued.

Effective doses of analogues or metabolites of midostaurin may be determined by the health care professional.

In another embodiment the subject is of a pediatric age. In another embodiment the subject is 0-18 years of age. In another embodiment, the subject is a newborn. In one embodiment, the subject is between 0 and 2 months of age. In another embodiment, the subject is a newborn. In one embodiment, the subject is between 0 and about 2 months of age. In one embodiment, the subject is between 0 and 1 year of age. In one embodiment, the subject is between 0 and about 1 year of age. In one embodiment, the subject is between 0 and 4 years of age. In one embodiment, the subject is between 0 and about 4 years of age. In another embodiment, the subject is a baby. In one embodiment the subject is a child. In one embodiment the subject is a toddler. In another embodiment the subject is an infant.

Clinical improvement of resolution may be assessed by the reduction or disappearance of symptoms, such as but not limited to bullae, skin blistering, flushing episodes, and elevated serum tryptase activity. Because mastocytosis in the pediatric population is mostly restricted to skin, in one embodiment, administration of midostaurin may be discontinued when resolution of bullae occurs.

Improvement may also be assessed by serum tryptase levels. Tryptase is an enzyme that is released from mast cells along with histamine and other substances. Tryptase levels can be significantly and persistently increased with mastocytosis. Normal serum tryptase levels are less than 5 ng/ml in pediatric subjects, and levels exceeding about 20 ng/ml are seen in mastocytosis; serum levels may be several hundreds of ng/ml. In one embodiment, a diagnosis of mastocytosis is made by determining serum tryptase levels in a pediatric subject's blood, and midostaurin therapy is initiated if the levels are above 30 ng/ml. Standard of care therapy may be administered as well. In one embodiment, both the resolution of bullae and return of serum tryptase levels to near normal levels is an indication that midostaurin therapy can be discontinued.

The following example is presented in order to more fully illustrate the preferred embodiments of the invention. It should in no way be construed, however, as limiting the broad scope of the invention.

EXAMPLES

Figure 3:
FIG. 3 shows fetal ultrasound at 35 weeks' gestation demonstrating two suspected bullae on the face (indicated by arrows).
Figure 4:
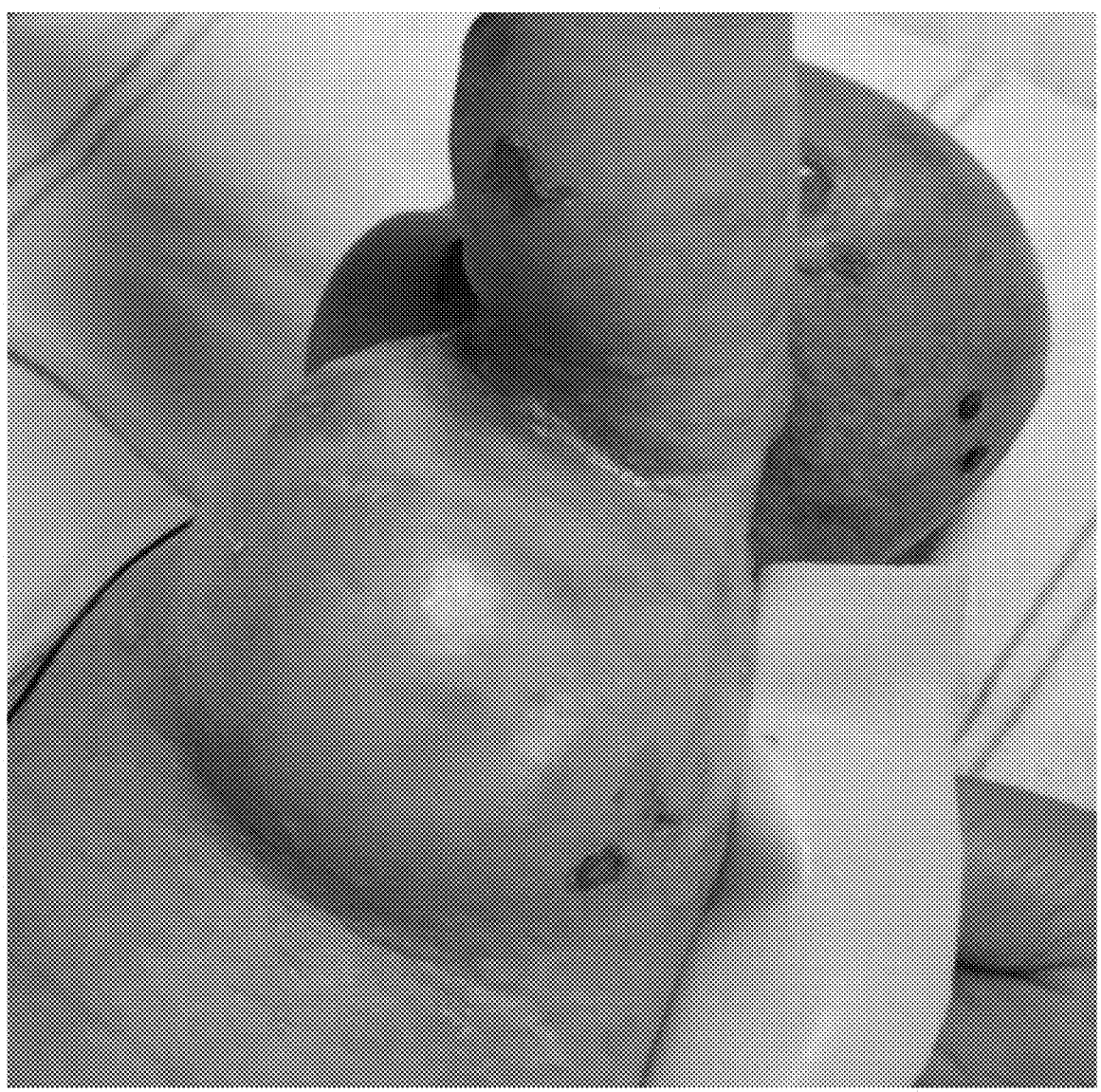
FIG. 4 shows patient at six months with large axillary fluid collection before drainage.

A full-term female had an uncomplicated prenatal course except for an ultrasound showing bullae on the face (FIG. 3). At birth a few, scattered bullae on her scalp were noted. Over weeks, more bullae developed on the face and torso. A biopsy of the skin at 3 weeks demonstrated mast cell aggregates and led to an initial diagnosis of cutaneous mastocytosis. She was treated with daily antihistamines, cromolyn, and montelukast. At age 6 months, she developed many painful, hemorrhagic bullae on light touch or skin trauma. Regions of her back and legs showed thickened, leathery skin (FIG. 1A and FIG. 1B). Flushing and diarrheal episodes increased despite treatment. She also developed a fluctuant, axillary mass (~8 cm diameter) (FIG. 4), for which she was admitted for further workup.

Laboratory studies showed leukocytosis, mild microcytic anemia, thrombocytosis, and hypoalbuminemia. The serum tryptase level was 187 mg/L (normal, <13 mg/L). Intravenous antibiotics were given. The axillary fluid collection was proximal to a necrotic lymph node (LN). Aggregates of spindled mast cells were noted in the subcapsular space of the LN and in the soft tissue around the LN. The fluid collection was drained to reveal serosanguinous fluid with no mast cells and no growth on culture. Seromas are rare findings in patients with SM, and it was speculated that it arose because of a combination of lymphatic injury due to destruction of the LN architecture (e.g., seen after postsurgical LN dissection of the axilla), mast-cell-mediated capillary leakage, and the large capacity of the axillary space. The bone marrow was hypercellular and showed approximately 5% accumulation of mast cells that were CD25+, with nearby aggregates of lymphocytes and slight megakaryocytosis (FIG. 1E and FIG. 1F). No hepatosplenomegaly was noted on imaging. Sequencing of the KIT gene from bone marrow tissue revealed the p.D816V pathogenic variant. In contrast, sequencing of whole blood for KIT revealed only the wild-type sequence. Given lack of hepatosplenomegaly, less than 30% mast cell burden in the bone marrow, no cytopenias, and no end-organ dysfunction, the patient was diagnosed with indolent SM.

One month later, she presented with worsening of the bullae, uncontrollable pruritus, irritability, and episodes of flushing despite continuation of therapy. The axillary fluid reaccumulated. She had worsening anemia, persistent thrombocytosis, low albumin, and low potassium. Her serum tryptase peaked at 267 mg/L. She received intravenous antibiotics and methylprednisolone (2 mg/kg/d) without improvement. The axillary fluid was drained again, with no mast cells seen. We started the patient on midostaurin, after informed consent with an institutional review board approved protocol, approval of the Food and Drug Administration in the form of an emergency investigational new drug application, and "compassionate use" approval by the manufacturer, we obtained a liquid formulation of midostaurin. We gave 30 mg/m2 twice daily, with prophylactic ondansetron given before each dose. She showed a modest response, with some decrease in skin blistering, decrease in flushing episodes, and down-trending tryptase levels. Over the next 2 months, because of persisting symptoms and still-elevated tryptase levels, we increased the dose of midostaurin to 45 mg/m2 twice daily, and later 60 mg/m2 twice daily, on the basis of recommendation of the manufacturer and a report of midostaurin use in children with relapsed acute leukemia.

Figure 2:
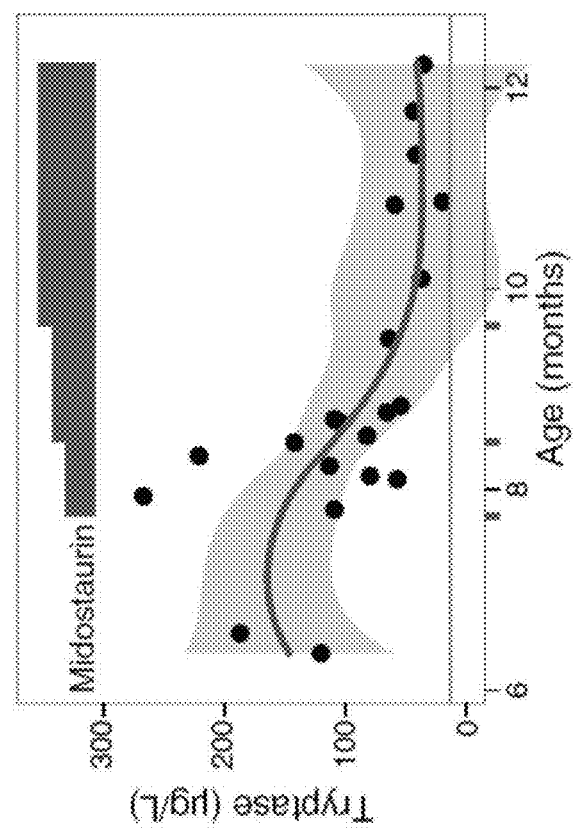
FIG. 2 shows the patient's serum tryptase levels (black) over time, with locally weighted smoothing (blue) and 95% CI (gray). The adult upper limit of normal is 13 mg/L (horizontal line). Treatment with midostaurin at doses of 30, 45, and 60 mg/m2 is indicated by the bars at the top and the ticks along the horizontal axis.

After 12 weeks, she showed significant clinical improvement with total resolution of bullae (FIG. 1C, FIG. 1D) and a decrease in serum tryptase levels down to nearly normal (FIG. 2). She has had no re-accumulation of her axillary fluid. She remained on H1 and H2 blockers, cromolyn, and montelukast; corticosteroids were weaned and discontinued; and her hydroxyzine dose has been halved. She has continued to have mild anemia and thrombocytosis. The origin of her persistent thrombocytosis is still unclear, but may represent an early sign of abnormal myelopoiesis that has been reported when SM advances to a myeloproliferative neoplastic disorder. She also has occasional and unexplained bruising, which may represent platelet or capillary dysfunction.

Generally, the patient is tolerating midostaurin well. Common side effects of midostaurin are nausea, vomiting, diarrhea, and thrombocytopenia. She has intermittent emesis, which is temporally unrelated to the administration of midostaurin; however, she has remained well hydrated and is growing along her growth curve.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating systemic mastocytosis in a pediatric subject in need thereof, comprising administering to the subject an effective dosing regimen comprising midostaurin.

2. The method of claim 1 wherein the pediatric subject is an infant.

3. The method of claim 1 wherein the mastocytosis is congenital or prenatal.

4. The method of claim 1 wherein the mastocytosis comprises the Kit D816V mutation.

5. The method of claim 1 wherein the mastocytosis is indolent.

6. The method of claim 1 wherein the mastocytosis is cutaneous mastocytosis.

7. The method of claim 1 wherein the systemic mastocytosis is indolent systemic mastocytosis, smoldering systemic mastocytosis, systemic mastocytosis with associated hematological neoplasm, aggressive systemic mastocytosis or mast cell leukemia.

8. The method of claim 1 wherein the mastocytosis is not responsive to standard of care therapy.

9. The method of claim 4 wherein standard of care comprises antihistamines, cromolyn, montelukast, antibiotics or corticosteroids, or any combination thereof.

10. The method of claim 1 wherein the midostaurin is administered twice daily at a dose of 30 mg/m$^2$, 45 mg/m$^2$ or 60 mg/m$^2$, or any combination or regimen thereof.

11. The method of claim 1 wherein the midostaurin is administered orally.

12. The method of claim 1 wherein the midostaurin is administered as a liquid formulation.

13. The method of claim 1 wherein ondansetron was administered prophylactically with each dose of midostaurin.

14. The method of claim 1 wherein the midostaurin administration reduces bullae, reduces skin blistering, reduces skin flushing, reduces serum tryptase levels, or any combination thereof.

15. The method of claim 1 wherein administration of midostaurin is discontinued when clinical improvement occurs.

16. The method of claim 1 wherein administration of midostaurin is discontinued when clinical improvement of systemic mastocytosis occurs.

17. The method of claim 16 wherein clinical improvement is reduction or elimination of bullae, reduction or elimination of skin blistering reduction or elimination of skin flushing, or the combination thereof.

18. The method of claim 16 wherein administration of midostaurin is discontinued when serum tryptase levels return to near or at baseline values.

19. The method of claim 1 wherein administration of midostaurin is discontinued when reduction of elimination of bullae is observed, reduction or elimination of skin blistering is observed, reduction or elimination of skin flushing is observed, a return to near normal or normal levels of serum tryptase occurs, or any combination of any of the foregoing.

20. The method of claim 1, wherein the subject is between 0 and 18 years of age, between 0 and about 18 years of age, between 0 and 2 months of age, between 0 and about 2 months of age, between 0 and 1 year of age, between 0 and about 1 year of age, between 0 and 4 years of age, or between 0 and about 4 years of age.

\* \* \* \* \*